United States Patent
Tham

(10) Patent No.: US 9,504,797 B2
(45) Date of Patent: Nov. 29, 2016

(54) SYSTEM AND METHOD OF PREDICTING $CO_2$ BREAKTHROUGH AND ABSORBENT REPLACEMENT

(71) Applicant: General Electric Company, Schenectady, NY (US)

(72) Inventor: Robert Q. Tham, Madison, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 304 days.

(21) Appl. No.: 14/145,540

(22) Filed: Dec. 31, 2013

(65) Prior Publication Data
US 2015/0182711 A1 Jul. 2, 2015

(51) Int. Cl.
| | |
|---|---|
| A61M 16/00 | (2006.01) |
| A61M 16/01 | (2006.01) |
| A61M 16/22 | (2006.01) |
| A61M 16/10 | (2006.01) |
| B01D 53/04 | (2006.01) |

(52) U.S. Cl.
CPC ..... *A61M 16/0051* (2013.01); *A61M 16/0057* (2013.01); *A61M 16/01* (2013.01); *A61M 16/104* (2013.01); *A61M 16/22* (2013.01); *B01D 53/0454* (2013.01); *A61M 2205/3303* (2013.01); *A61M 2205/502* (2013.01); *A61M 2230/005* (2013.01); *A61M 2230/432* (2013.01); *B01D 2257/504* (2013.01); *B01D 2259/4533* (2013.01); *Y02C 10/08* (2013.01)

(58) Field of Classification Search
CPC ......... A61M 16/0051; A61M 16/104; A61M 16/22; A61M 16/0057; A61M 16/01; A61M 2205/3303; A61M 2230/005; A61M 2205/502; A61M 2230/432; B01D 53/0454; B01D 2259/4533; B01D 2257/504; Y02C 10/08

USPC ............ 128/205.12, 205.28, 205.22, 204.22, 128/200.24, 202.22, 202.27, 205.23, 205.27
See application file for complete search history.

(56) References Cited

U.S. PATENT DOCUMENTS

| | | | |
|---|---|---|---|
| 7,148,806 B2 * | 12/2006 | Anttila | A61M 16/22 128/205.12 |
| 7,987,849 B2 * | 8/2011 | Heesch | A61M 16/0045 128/204.18 |
| 7,997,268 B1 | 8/2011 | Leonard et al. | |

FOREIGN PATENT DOCUMENTS

| | | | | |
|---|---|---|---|---|
| DE | WO2006099863 A1 * | 3/2006 | | A61B 7/08 |
| DE | 102006051571 B3 | 2/2008 | | |
| EP | 1579884 A1 | 9/2005 | | |

OTHER PUBLICATIONS

Google translation of EP1861173 which is a family member of WO2006099863A1.*
International Search Report and Written Opinion for corresponding PCT application No. PCT/US2014/050555 dated Oct. 31, 2014; 11 pages.

* cited by examiner

*Primary Examiner* — Tan-Uyen (Jackie) T Ho
*Assistant Examiner* — Mark Wardas

(57) ABSTRACT

The system and method of the present application predicts if there is sufficient $CO_2$ absorbent capacity for the next anesthesia case. If insufficient, the canister can be preemptively replaced when no patient is connected to the breathing system. Such prediction also allows clinicians to determine if the $CO_2$ canister has to be changed during the present case or to wait until the end of the case. In the latter, the clinician may buy time by increasing the fresh gas flow rate to reduce the amount of patient $CO_2$ gases recirculated. A predictive estimation of $CO_2$ breakthrough allows more time to prepare for an orderly $CO_2$ canister replacement during a quiet period in the anesthesia care.

18 Claims, 4 Drawing Sheets

SYSTEM AND METHOD OF PREDICTING CO₂ BREAKTHROUGH AND ABSORBENT REPLACEMENT

FIELD

The present application is directed to the field of patient ventilators. More specifically, the present application is directed to ventilator circuit carbon dioxide ($CO_2$) removal.

BACKGROUND

A circle system is used to ventilate patients undergoing general anesthesia. To minimize wastage of excess expired anesthetic breathed out by the patient, the circle breathing system is designed to enable patient expired gases to be rebreathed after carbon dioxide is removed using $CO_2$ absorbent. In addition, oxygen and anesthetic agent is replenished to maintain desired concentration of gases breathed by the patient. $CO_2$ absorbent housed in a canister has a finite capacity to remove $CO_2$ from the expired patient gases. They can be replaced at the start of day or end of day on a routine basis. This is wasteful as unused absorbent capacity is discarded.

Alternatively, the absorbent is replaced during an anesthesia case when it is spent. This is detected by measurement of significant inspired $CO_2$ concentration. A typical threshold value is 0.5% of sustained inspired $CO_2$ concentration. This cost saving practice exposes the patient while unconscious and requires mechanical ventilation assistance during anesthesia, where the risk is disruption of ventilation that include temporarily pausing ventilation, disconnecting the breathing system, installing a $CO_2$ canister with fresh absorbent, checking the integrity of the reconnected breathing system, and resuming ventilation.

Dye with color changes in the presence of $CO_2$ is also used to indicate sent absorbent, as is computation of remaining $CO_2$ absorption capacity based on the absorbent refilled quantity and rate of $CO_2$ recirculated. Since quantity of refill and efficiency of the packed absorbent is a poor estimate of usable absorbent, the estimator/gauge is inaccurate.

SUMMARY

The above-mentioned shortcomings, disadvantages and problems are addressed herein which will be understood by reading and understanding the following specification.

The system and method of the present application predicts if there is sufficient $CO_2$ absorbent capacity for the next anesthesia case. If insufficient, the canister can be preemptively replaced when no patient is connected to the breathing system. Such prediction also allows clinicians to determine if the $CO_2$ canister has to be changed during the present case or to wait until the end of the case. In the latter, the clinician may buy time by increasing the fresh gas flow rate to reduce the amount of patient $CO_2$ gases recirculated. A predictive estimation of $CO_2$ breakthrough allows more time to prepare for an orderly $CO_2$ canister replacement during a quiet period in the anesthesia care.

In one aspect of the present application, a computerized method of predicting carbon dioxide ($CO_2$) breakthrough in an anesthesia ventilator comprises inputting into a computing system a pre-determined minimum threshold for a minimum averaged inspired $CO_2$ concentration ($FiCO_2$) and a $CO_2$ absorbent replacement, inputting into the computing system a set of data received from the anesthesia ventilator, wherein the set of data includes a measured $FiCO_2$, determining whether the measured $FiCO_2$ exceeds the pre-determined minimum threshold, extrapolating, a number of breaths for the measured $FiCO_2$ to reach the $CO_2$ absorbent replacement threshold, and calculating a $CO_2$ absorbent replacement time with the number of breaths and a breaths interval time.

In another aspect of the present application, a non-transitory computer readable medium including instructions that, when executed on a computing system, cause the computing system to receive from a user interlace a pre-determined minimum threshold for a minimum averaged inspired $CO_2$ concentration ($FiCO_2$) and a $CO_2$ absorbent replacement, receive a set of data from the anesthesia ventilator, wherein the set of data includes a measured $FiCO_2$, determine whether the measured $FiCO_2$ exceeds the pre-determined minimum threshold, extrapolate a number of breaths for the measured $FiCO_2$ to reach the $CO_2$ absorbent replacement threshold, and calculate a $CO_2$ absorbent replacement time with the number of breaths and a breaths interval time.

In another aspect of the present application, an anesthesia ventilator comprises a $CO_2$ canister containing $CO_2$ absorbent, a computing system including the storage device and a processor, the storage device including instructions that, when executed on the processor, cause the computing system to receive from a user interface a pre-determined minimum threshold for a minimum averaged inspired $CO_2$ concentration ($FiCO_2$) and a $CO_2$ absorbent replacement for the $CO_2$ absorbent, receive a set of data from the anesthesia ventilator, wherein the set of data includes a measured $FiCO_2$, determine whether the measured $FiCO_2$ exceeds the pre-determined minimum threshold, extrapolate a number of breaths for the measured $FiCO_2$ to reach the $CO_2$ absorbent replacement threshold, wherein the extrapolation utilizes a set of predetermined parameters, and calculate a $CO_2$ absorbent replacement time with the number of breaths and a breaths interval time, and output the $CO_2$ absorbent replacement time to a user interface.

DETAILED DESCRIPTION

In the present description, certain terms have been used for brevity, clearness and understanding. No unnecessary limitations are to be applied therefrom beyond the requirement of the prior art because such terms are used for descriptive purposes only and are intended to be broadly construed. The different systems and methods described herein may be used alone or in combination with other systems and methods. Various equivalents, alternatives and modifications are possible within the scope of the appended claims. Each limitation in the appended claims is intended to invoke interpretation under 35 U.S.C. §112, sixth paragraph, only if the terms "means for" or "step for" are explicitly recited in the respective limitation.

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
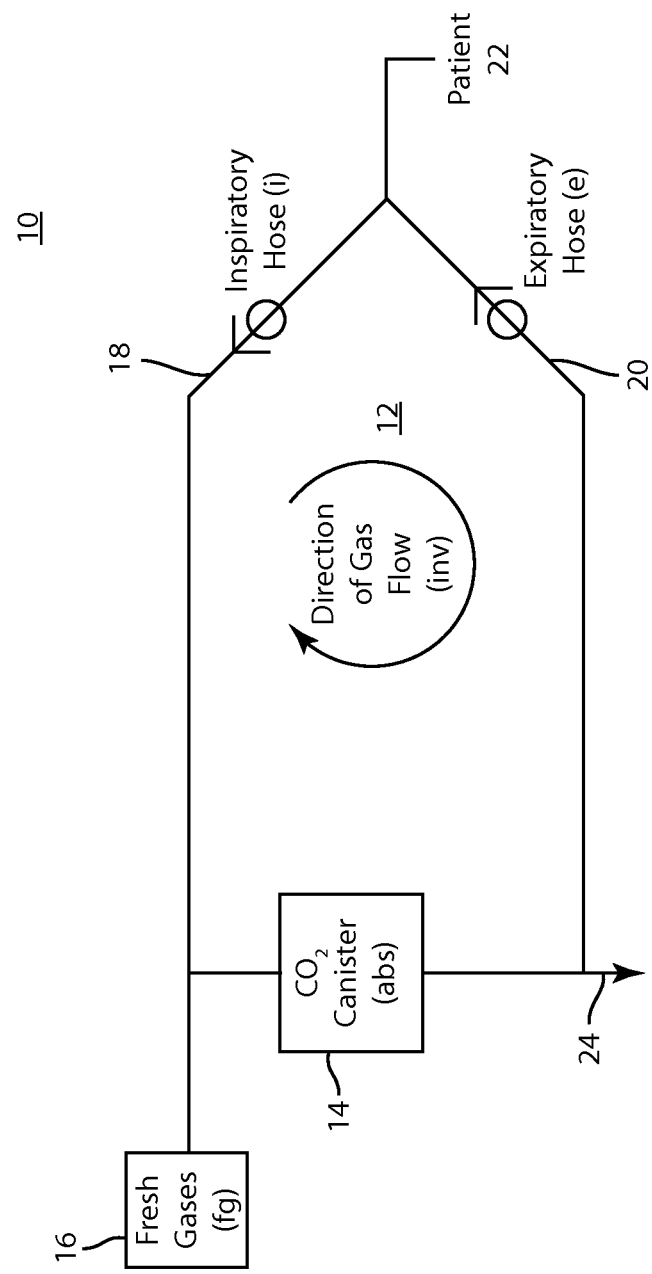
FIG. 1 is a schematic illustration of a breathing circuit illustrating an embodiment of the present application.

Referring to FIG. 1, the system and method of the present application relates to an anesthesia ventilator 10 with a circle breathing system 12 having a $CO_2$ canister 14 with absorbent (abs). The patient 22 is ventilated via mechanically through a volume reservoir (e.g. bellows, inflatable bag, long gas conduit) or manual bag (not shown). Concentrations of inspired and expired gases breathed by the patient 22 are monitored by a gas monitor (not shown). Gas concentrations measured include $O_2$, $CO_2$, $N_2O$, air, and anesthetic gas. Inspired and expired gas flows are measured and gas volumes are computed by integrating the flow over a breath. As in any circle anesthesia breathing system 12, fresh gases (FG) 16 are added to replenish gases consumed by the patient 22. Excess FG 16 that is not consumed by the patient 22 is exhausted via an exhaust (exh) 24 having a pop off valve. Recirculated expired $CO_2$ passes through the $CO_2$ canister 14 and are absorbed by the $CO_2$ abs. As absorbent is spent, some $CO_2$ passes through the $CO_2$ canister 14 and is diluted by the FG 16 to form part of the inspired patient 22 gases. The measured concentration of inspired $CO_2$ is reported to a computing system 200 that predicts the rate of concentration increase of $CO_2$ breakthrough.

Figure 2:
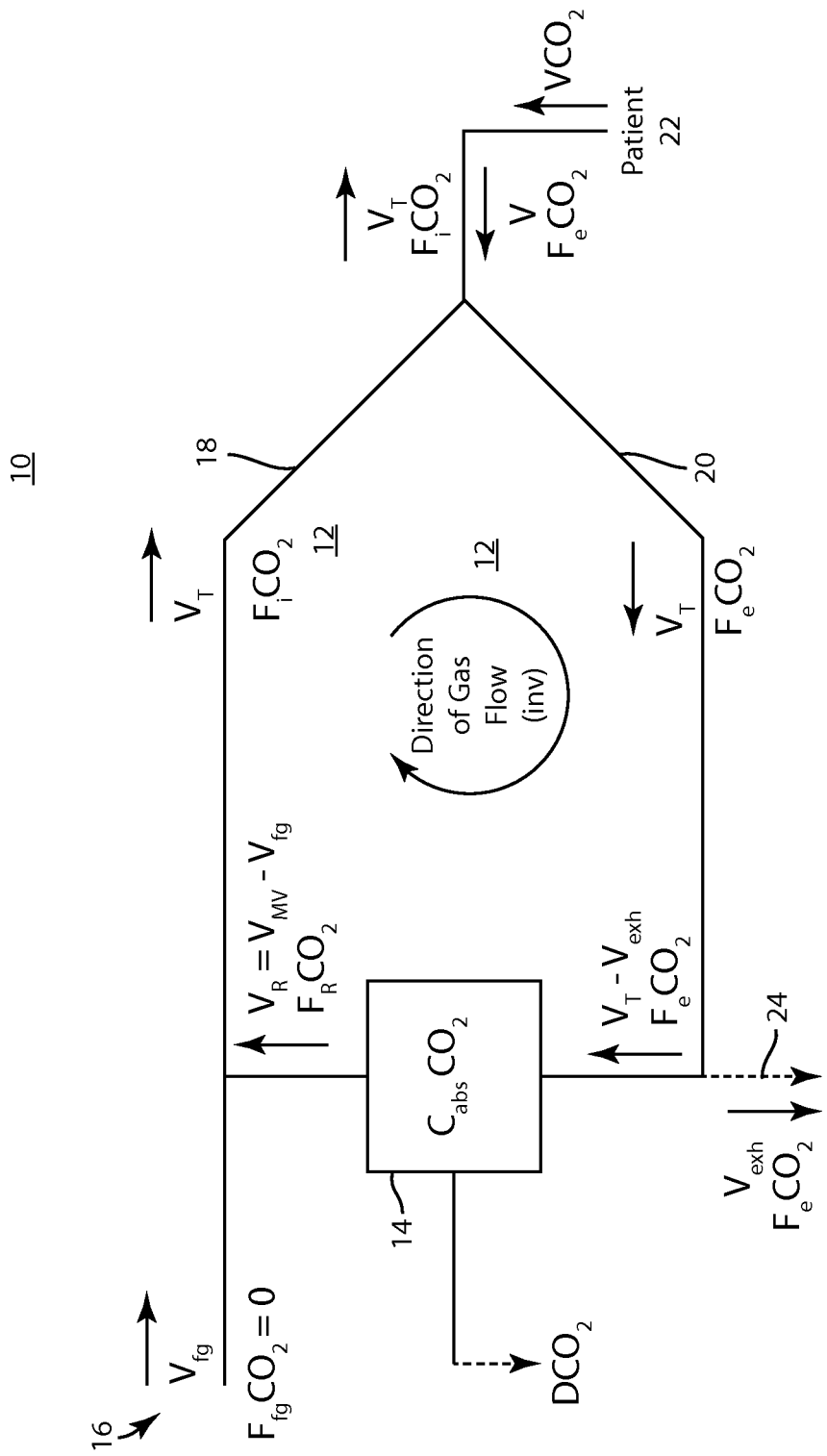
FIG. 2 is a schematic illustration of a breathing circuit illustrating an embodiment of the present application.

Referring to FIG. 1, the anesthesia ventilator 10 includes a circle breathing system 12 as stated above. The circle breathing system 12 includes an expiratory hose 20, the inspiratory hose 18, and the $CO_2$ canister 14, that make up the main portion of the circle breathing system 12. The circle breathing system 12 further includes the breathing hose that leads to the patient 20, as well as the fresh gases 16 source and the exhaust 24. As pictures in FIG. 1, the gases flow in a clockwise direction in the circle breathing system 12 shown in FIG. 1, and the hose that connects the patient 22 to the circle breathing system 12 allows gas flow to and from the circle breathing system 12 as shown in FIG. 2. Gas flows in the circle breathing system is directed by two one-way valves typically located in line with the inspiratory (18) and expiratory (20) breathing hoses. The fresh gases 16 source flowing from a high pressure supply flow one-way direction into the circle breathing system 12. Likewise, the exhaust 24 allows one-way flow to ambient or scavenging and away from the circle breathing system 12 which is positively pressured during ventilation. In high flow recirculating anesthesia system a blower fan (flowing in excess of 50 lpm) determines the unidirectional flow of the recirculating gas flows.

Referring to FIG. 2, it should be noted that all of the references to the various formulas and abbreviations will be described and defined in the following description. Furthermore, it should be noted that the arrows included in the circle breathing system 12 of FIG. 2 are illustrative of gas flow direction of the circle breathing system 12.

As stated above, current dye solutions to indicate spent absorbent are imprecise and the dye color changes tend to regenerate. Predicting $CO_2$ expenditure of absorbent based on recirculated $CO_2$ without considering $CO_2$ concentration breakthrough is associated with error from uncertain absorption capacity based on quantity of absorbent refilled. Inefficiencies in the $CO_2$ absorption such as channeling, operating temperatures that contribute to this uncertainty.

However, the system and method of the present application utilizes the actual breakthrough $CO_2$ concentration to extrapolate the instance when a threshold $CO_2$ will be reached given current or what if operating setting of the breathing system.

Knowing when and if the absorbent in the $CO_2$ canister 14 can last through the next case allows the canister 14 to be replaced when the patient 22 is not connected between anesthesia cases, and when the canister 14 will not last through the next anesthesia case Referring now the FIGS. 1 and 2, the derivation of Gas Exchange in the System will be determined as follows:

First considering the gas exchange in the lungs; inspired gases breathed into the lungs equal expired gases breathed out of the lungs plus gas entering or leaving the lungs from pulmonary blood. Applying conservation of mass to $CO_2$ exchange over a breath;

Inspired $CO_2$ volume=expired $CO_2$ volume+$CO_2$ from blood or $V_T \times FiCO_2 = V_T \times FeCO_2 + VCO_2$, where $V_T$ is the tidal volume per breath (in mL/min), $FiCO_2$ is the averaged inspired $CO_2$ concentration, and $VCO_2$ is the $CO_2$ production (in mL/min), in other words, $CO_2$ from the pulmonary blood. The product of tidal volume ($V_T$) and respiratory rate per minutes yield minute ventilation $$\text{Rearranging } (FeCO)_2 = (FiCO)_2 - \frac{VCO_2}{V_T} \qquad (1)$$

Still referring to FIGS. 1 and 2, the movement of $CO_2$ in the circle breathing system 12 over a breath inspired and expired gas movement to the patient 22 are transported by the ventilator 10 at the rate of minute ventilation which is the product of tidal volume (VT) and respiratory rate per minute. In some high flow recirculating ventilators, the recirculating flows can be much higher than minute ventilation. However, the effective flow of gas exchange with the lungs remains at the rate of minute ventilation. As such, the high flow recirculation helps to even out gas concentration in the circle breathing system 12 but has the same effective gas exchange rate with the patient 22 and consumption of $CO_2$ absorbent, and is thus considered as equivalent in its gas exchange over a breath as the conventional circle system 12.

Still referring to FIGS. 1 and 2, the movement of $CO_2$ through the $CO_2$ canister 14 per breath includes applying from the law of conservation applied over a breath, where inflow of $CO_2$ into the canister 14 equals outflow of $CO_2$ from the canister 14 plus $CO_2$ absorbed by the $CO_2$ absorbent in the canister 14. Inflow of $CO_2$ into the absorber 14 equals $CO_2$ expired by the patient 22 less $CO_2$ exhausted via the exhaust 24, so $$\text{volume} = V_T \times FeCO_2 - V_{exh} \times FeCO_2 \qquad (2)$$

$$= (V_T - V_{exh}) \times FeCO_2$$

where $FeCO_2$ is the average patient 22 expired gases. $FeCO_2$ can be derived from the end tidal $CO_2$ measured using a gas monitor, which is used routinely as a standard of anesthesia care, and using the formula $$FeCO_2 = E_T CO_2 \left(1 - \frac{V_D}{V_T}\right),$$

where $E_T CO_2$ is the measured end tidal $CO_2$ and $V_D$ is the deadspace per breath and the ratio of $$\frac{V_D}{V_T}$$

is typically about 10 to 20%. The outflow of $CO_2$ from the canister $14 = V_R \times F_R CO_2$, where $V_R$ = tidal volume to the patient 22 less the fresh gas flow in a breath interval ($Vfg$)

$= V_T - V_{fg}$, and is the total gas flow from the $CO_2$ absorber.

Now, substituting gas flow into the $CO_2$ flow through the $CO_2$ canister 14 yields:

$$(V_T - V_{exh}) \times FeCO_2 = (V_T - V_{fg}) \times F_R CO_2 + DCO_2,$$

where $DCO_2$ is the $CO_2$ absorbed by the $CO_2$ canister 14 over the breath time. Rearranging and solving for $F_R CO_2$ yields:

$$F_R CO_2 = \frac{\left(1 - \frac{V_{exh}}{V_T}\right) \times FeCO_2 - \frac{DCO_2}{V_T}}{\left(1 - \frac{V_{fg}}{V_T}\right)} \quad (3)$$

Considering the confluence of fresh gas 16 and $CO_2$ outflow of the $CO_2$ canister 14 where the fresh as 14 free of $CO_2$ dilutes the recirculating $CO_2$ concentration from the $CO_2$ canister 14 to yield the inspired $CO_2$ concentration ($FiCO_2$):

$$V_R \times F_R CO_2 + V_{fg} \times F_{fg} CO_2 = V_T \times FiCO_2 \quad (4)$$

Since fresh gas is free of $CO_2$, $F_{fg} CO_2 = 0$ yielding:

$$V_R \times F_R CO_2 = V_T \times FiCO_2$$

Substituting $V_R = V_T - V_{fg}$ and rearranging yields:

$$F_R CO_2 = \frac{F_i CO_2}{\left(1 - \frac{V_{fg}}{V_T}\right)} \quad (5)$$

Further substitute (5) into (3) and solving for $F_i CO_2$ yields:

$$(FiCO_2) = \left(1 - \frac{V_{exh}}{V_T}\right) FeCO_2 - \frac{DCO_2}{V_T} \quad (6)$$

Still referring to FIG. 2, since $V_{exh}$ is the net excess gas volume popped off from the circle breathing system 12 and the net excess gas volume is made up of fresh gas 16, patient $CO_2$ production, $O_2$ uptake (metabolism), agent exchange and $CO_2$ absorbed by the $CO_2$ canister 14. $V_{exh}$ can be derived from the equation:

$$V_{exh} = V_{CO_2} - DCO_2 + V_{fg} - V_{O_2} - V_{AX} \quad (7)$$

During anesthesia maintenance phase, $V_{CO_2}$, $V_{O_2}$ fairly constant and at agent equilibrium the agent uptake $V_{AX}$ is fairly constant and small compared to $V_{CO_2}$ and $V_{O_2}$. For simplicity, let $V_C$ represent the net gas exchange from the fresh gas and the patient, i.e.:

$$V_C = V_{fg} + V_{CO_2} - V_{O_2} - V_{AX}, \text{ and}$$

substituting $V_C$ into (T) and (6) yield:

$$(FiCO_2)_2 = \left(1 - \frac{V_C - DCO_2}{V_T}\right) FeCO_2 - \frac{DCO_2}{V_T} \quad (8)$$

$$= \left(1 - \frac{V_C}{V_T}\right) FeCO_2 - \frac{DCO_2}{V_T}(1 - FeCO_2)$$

or $$(FiCO_2)_2 = \left(1 - \frac{V_C}{V_T}\right) FeCO_2 - \frac{DCO_2}{V_T}$$

since $FeCO_2 \cong 0.05 \ll 1$.

Considering a sequence of regular breathing during anesthesia, leading, up to the $n^{th}$ breath where the $V_T$ and $V_{CO_2}$ remain constant is:

$$V_T^n = V_T^{n-1} = \ldots = V_T \text{ and } V_{CO_2}^{n-1} = \ldots V_{CO_2}$$

At $CO_2$ break through, $DCO_2$ decreases as additional $CO_2$ is absorbed in each break.

From C1 we have:

$$Fe^n CO_2 = Fi^n CO_2 - \frac{V^n CO_2}{V_T^n} \quad (9)$$

$$\text{or } Fe^n CO_2 = Fi^n CO_2 - \frac{VCO_2}{V_T}$$

From C8 we have:

$$Fi^n CO_2 = \left(1 - \frac{VC}{VT}\right) Fe_{CO_2}^{n-1} - \frac{D^n CO_2}{V_T^n} \quad (10)$$

or $$Fi^n CO_2 = \left(1 - \frac{VC}{VT}\right) Fe^{n-1} CO_2 - \frac{D^n CO_2}{VT}$$

That is new inspired $FiCO_2$ concentration is the result of circulating the partially exhausted and absorbed patient $CO_2$ breath and further diluted by the fresh gas 16. Since $Fi^n CO_2$, $Fe^{n-1} CO_2$, $V_C$, $VT$ are measured, set or approximately known, $D^n CO_2$ can be computed as:

$$D^n CO_2 = \left\{\left(1 - \frac{VC}{VT}\right) Fe^{n-1} CO_2 - Fi^{n-1} CO_2\right\} * VT \quad (11)$$

At the previous (n−1) breath, $$Fi_{CO_2}^{n-1} = \left(1 - \frac{VC}{VT}\right) Fe_{CO_2}^{n-2} - \frac{D^{n-1} CO_2}{VT} \quad (12)$$

Depending on the design of the absorber canister 14, and the absorbent, at $CO_2$ breakthrough the rate of change of $CO_2$ depletion as the absorbent is spent can be constant, linearly or nonlinearly proportion to the remaining capacity of the $CO_2$ absorbent. In this description, assuming that the change in depletion rate per breath is a constant D or, $$D^{n-1}CO_2 = D^nCO_2 - D \tag{13}$$

In order to extrapolate and predict the responses of $FiCO_2$ and $FeCO_2$, $D^nCO_2$ and D must be solved. Substituting (13) into (12) yield:

$$Fi^{n-1}CO_2 = \left(1 - \frac{VC}{VT}\right)Fe^{n-2}CO_2 - \frac{D^nCO_2 - D}{VT} \tag{14}$$

Since $D^nCO_2$ can be found from equation (11), D can be computed using measured and approximated values of $Fe^{n-1}CO_2$, $Fe^{n-2}CO_2$, $V_C$, VT. With D known on a breath-to-breath basis the future response of $F_i^{n+k}CO2$ can be predicted using the following set of equations:

Applying equation (10) to predict k number of breaths into the future yield, $$Fi^nCO_2 = \left(1 - \frac{VC}{VT}\right)Fe^{n-1}CO_2 - \frac{D^nCO_2}{VT} \tag{15a}$$

$$Fi^{n+1}CO_2 = \left(1 - \frac{VC}{VT}\right)Fe^nCO_2 - \frac{D^nCO_2 + D}{VT} \tag{15b}$$

$$\vdots \tag{15}$$

or $$Fi^{n+k}CO_2 = \left(1 - \frac{VC}{VT}\right)Fe^{n+k}CO_2 - \frac{D^nCO_2 + kD}{VT} \tag{15k}$$

Likewise applying equation (9) to predict k number of breaths into the future yields, $$Fe^nCO_2 = Fi^nCO_2 + \frac{VCO_2}{VT} \tag{16a}$$

$$Fe^{n+1}CO_2 = Fi^{n+1}CO_2 + \frac{VCO_2}{VT} \tag{16b}$$

$$\vdots \tag{16}$$

or $$Fe^{n+k}CO_2 = Fi^{n+k}CO_2 + \frac{VCO_2}{VT}. \tag{16k}$$

The system of equations 15 and 16 can be iterated and solved sequentially to predict the $CO_2$ concentrations at the n+k breath, or the number of breaths k) needed to reach a concentration of $FiCO_2$ breakthrough.

In a particular example, assume that at breath n, the breakthrough inspired $CO_2$ $FiCO_2$ is at 0.1% and at breath n+k the breakthrough $CO_2$ is $Fi^{n+k}CO_2$ is 0.5%. The time for the $FiCO_2$ to rise from 0.1% to 0.5% is therefore k times the breath interval.

Note that the user can change the values of say Vfg, VT, $VCO_2$ or other related ventilations parameter to predict "what if" situations if these parameters are varied. Such variation is helpful to assist the clinician to adjust future values of ventilation or the fresh gas 16 setting to prolong or better estimate the duration of $CO_2$ breakthrough, and for the given $CO_2$ canister 14 be replaced.

For linear and non-linear proportional changes in the depletion rate of absorbent, a similar approach can be used to iteratively solve these two sets of equations to predict future responses of $FiCO_2$ breakthrough. In this case, several breaths leading to the nth breath may be required to solve for $D^nCO_2$ and the depletion profile of the absorbent.

Figure 3:
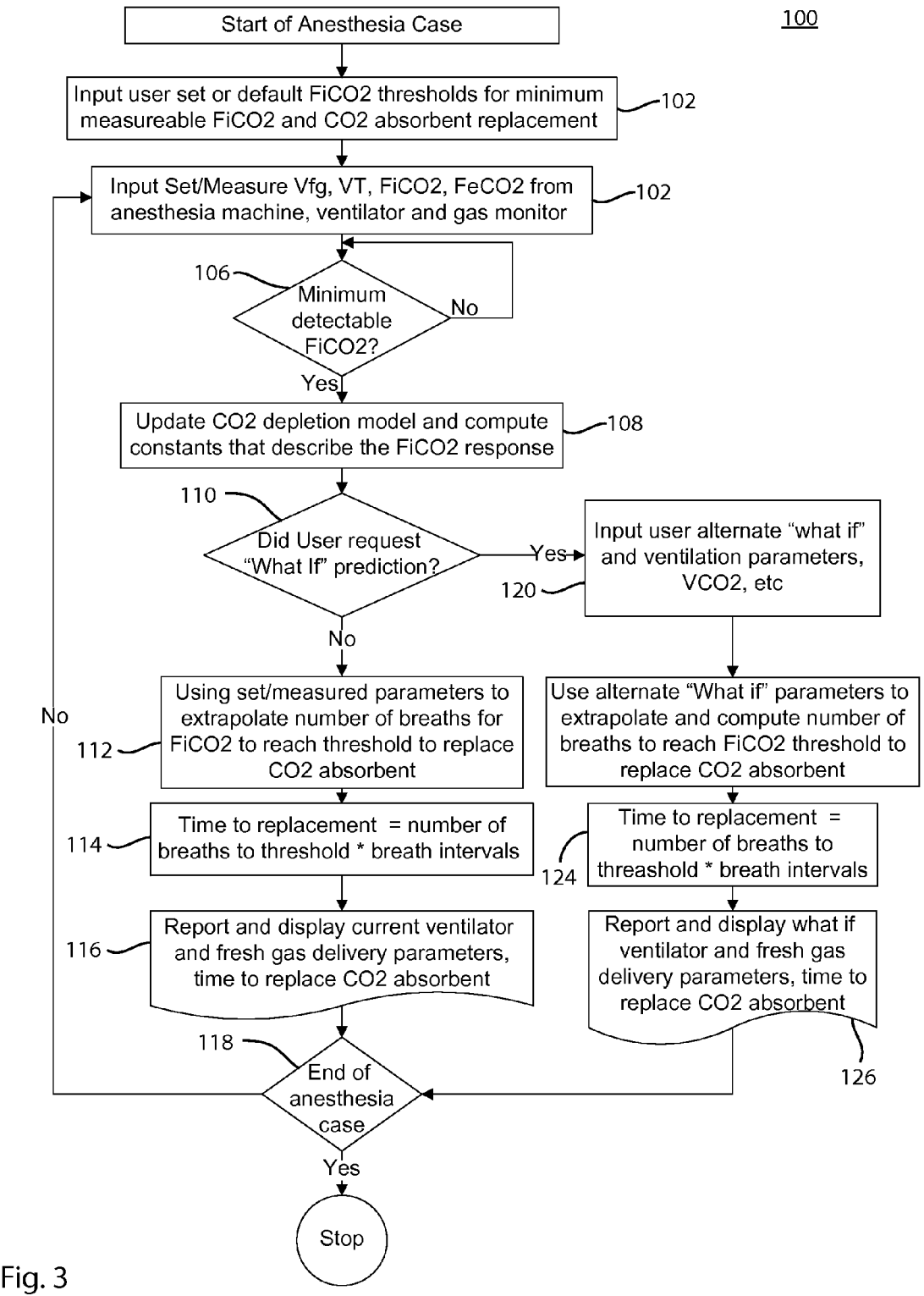
FIG. 3 is a flow chart illustrating an exemplary method in accordance with an embodiment of the present application.

Referring now to FIG. 3, a method of the present application is illustrated in the flow chart. In the method 100, at the start of an anesthesia case, users set or default $FiCO_2$ thresholds for minimum measureable $FiCO_2$ and $CO_2$ absorbent replacement R input. In step 104, $V_{fg}$, Vmv, $FiCO_2$, $FeCO_2$ from the anesthesia machine, ventilator and gas monitor are set and/or measured and inputted into the computing system. In step 106, if the minimum detectable $FiCO_2$ is met, then the method moves on to step 108. If the minimum detectable $FiCO_2$ is not met in step 106, then the method remains at step 106 until the minimum detectable $FiCO_2$ is obtained. In step 108, the $CO_2$ depletion model is updated and constants that describe the $FiCO_2$ response are computed, and in step 110, if the user does not request an "what if" prediction, then the method continues to step 112. It the user does request as "what if" predictions in step 110, then the method continues to step 120.

Still referring to the method 100, in step 120, the user alternate "what if" parameters are inputted. Examples of such inputs are fresh gas and ventilation parameters and the $CO_2$. In step 122, alternate "what if" parameters are used to extrapolate and compute the number of breaths to reach $FiCO_2$ threshold to replace the $CO_2$ absorbent. In step 124, the replacement time is determined based on the number of breaths to threshold times the breath intervals, and in step 126, the method reports and displays the "what if" ventilator and fresh gas delivery parameters, and time to replace the $CO_2$ absorbent. If this is the end of the anesthesia case in step 118, then the method ends. If this is not the end of the anesthesia case, then the method goes back to step 104.

Still referring to FIG. 3 and the method 100, in step 112 the set/measured parameters are used to extrapolate the number of breaths for $FiCO_2$ to reach a threshold to replace the $CO_2$ absorbent. In step 114, the time for replacement is calculated by the number of breaths to the threshold times the breath intervals, and in step 116, the current ventilator and fresh gas delivery parameters and time to replace the $CO_2$ absorbent are reported and displayed for the user. Once again, in step 118, if the end of the anesthesia case has been reached, then the method ends. However, if the end of the anesthesia case has not been reached, then the method continues in step 104.

Figure 4:
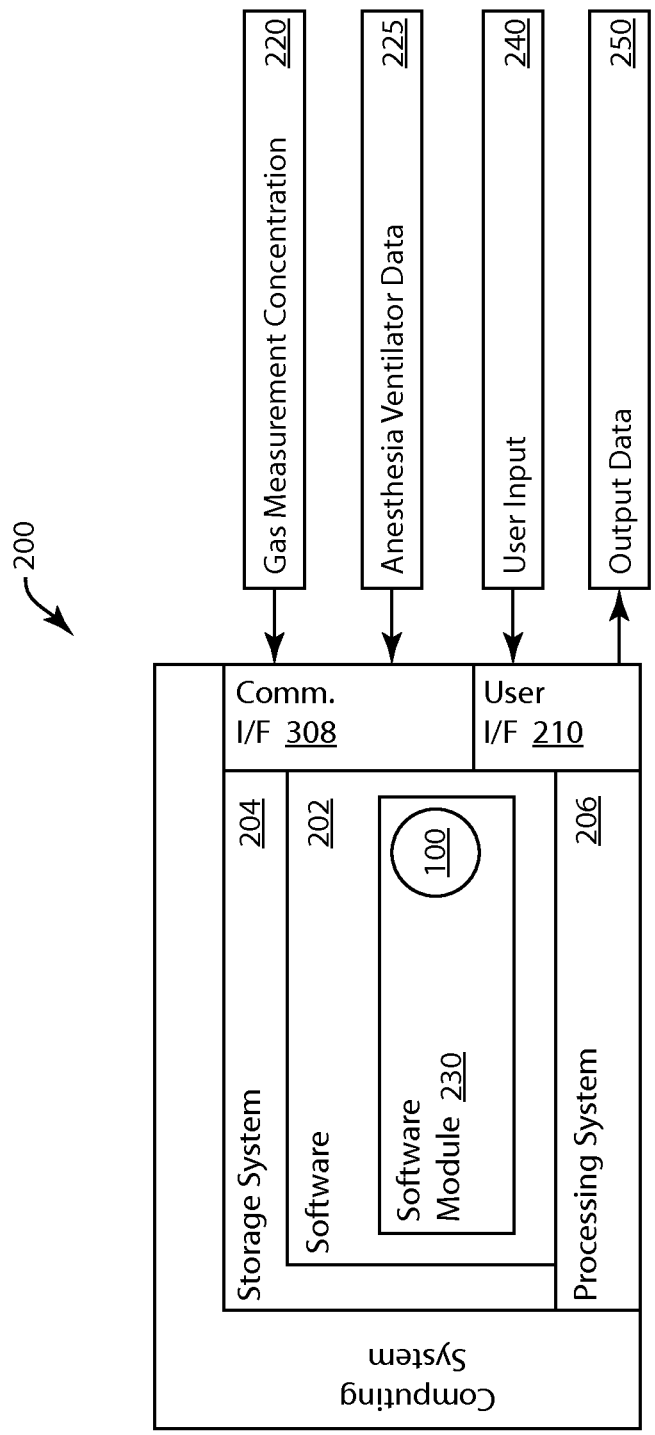
FIG. 4 is a block diagram illustrating an embodiment of the system of the present application.

FIG. 4 is a system diagram of an exemplary embodiment of as computing system 200 as may be used to implement embodiments of the method 100, or in carrying out embodiments of portions of the anesthesia ventilator 10. The computing system 200 includes a processing system 206, storage system 204, software 202, communication interface 208, and as user interface 210. The processing system 206 loads and executes software 202 from the storage system 204, including a software module 230. When executed by the computing system 200, software module 230 directs the processing system to operate as described herein in further detail in accordance with the method 200, or a portion thereof. It should be noted that the computing system 200 may be configured in a number of locations proximate or remote from the anesthesia ventilator 10. For example, the computing system 200 may be included in the ventilator 10 in the RFID reader 30, and/or in any user workstation proximate to the ventilator 150 or remote in a practitioner's station, care station, or other computer station.

Although the computing system 200 as depicted in FIG. 4 includes one application module 230 in the present example, it is to be understood that one or more modules could provide the same operations or that exemplary embodiments of the method 100 may be carried out by a plurality of modules 230. Similarly, while the description as provided herein refers to a computing system 200 and a processing system 206, it is to be recognized that implementations of such system can be performed by using one or more processors 206, which may be communicatively connected, and such implementations are considered with be within the scope of the description. Exemplarily, such implementations may be used in carrying out embodiments of the system 10 depicted in FIGS. 1 and 2.

Referring back to FIG. 4, the processing system 206 can comprise a microprocessor or other circuitry that retrieves and executes software 202 from storage system 204. Processing system 206 can be implemented within a single processing device but can also be distributed across multiple processing devices or sub-systems that cooperate in executing programming instructions. Examples of processing system 206 includes general purpose central processing units, application specific processor, and logic devices, as well as any other type of processing device, combinations of processing device, or variations thereof. The storage system 204 can include any storage media readable by the processing system 206 and capable of storing the software 202. The storage system 304 can include volatile and non-volatile, removable and non-removable media implemented in any method of technology for storage of information such as computer readable instructions, data structures, program modules or other data. Storage system 204 can be implemented as a single storage device but may also be implemented across multiple storage devices or sub-systems. Storage system 204 can further include additional elements, such as a controller capable of communicating with the processing system 206.

Examples of storage media include random access memory, read only memory, magnetic disc, optical discs, flash memory, virtual and non-virtual memory, magnetic sets, magnetic tape, magnetic disc storage or other magnetic storage devices or any other medium which can be used to store the desired information and that may be accessed by an instruction execution system, as well as any combination or variation thereof, or any other type of storage medium. In some implementations, the storage media can be a non-transitory storage media. It should be understood that in no case the storage media propagated signal.

User interface 210 can include a mouse, a keyboard, a voice input device, a touch input device for receiving a gesture from a user, a motion input device for detecting non-touch gestures, and other motions by a user, and other comparable input devices and associated processing elements capable of receiving user input from a user. User interface 210 can also include output devices such as a video display or a graphical display that can display an interface associated with embodiments of the systems and methods as disclosed herein. Speakers, printers, haptic devices, and other types of output devices may also be included in the user interface 210. The user interface 210 is configured to receive user inputs 240 which in non-limiting embodiments may be irregularity user preferences as disclosed in further detail herein. It is also understood that embodiments of the user interface 210 can include a graphical display that presents the reports or alerts as described in further detail herein.

As has been described in further detail herein, the communication interface 208 is configured to receive gas measurement concentrations 220. The anesthesia ventilator data 225 includes all data set of measured and utilized in the formulas discussed above with respect to FIG. 2. Accordingly, the gas measurement concentrations 220 and the rest of the anesthesia ventilator data 225 is inputted into the communication interface 208. User input 240 as described in the description of FIG. 2 and the method of FIG. 3, is input into the user interface 210. The computing system 200 processes the measured patient gas concentrations 220 including concentrations of inspired and expired $CO_2$, anesthesia ventilator data 225 and user input 240 according to the software 302 and method 100, and as described in detail herein to produce output data 250 which may be pushed to one or more users through the user interface 310. The output data 250 may include any analysis conducted by the computing system including current ventilator and fresh gas delivery parameters, time to replace $CO_2$ absorbent, "what if" ventilator and fresh gas delivery parameters, and "what if" time to replace $CO_2$ absorbent information. Further as described herein, the computing system 200 can output alerts, and/or reports 250 to the user, and may further accept user input 240, such as but not limited to, setting off of alerts, modifications of the reports, and other administration of the alerts and data.

While the invention has been described with reference to preferred embodiments, those skilled in the art will appreciate that certain substitutions, alterations and omissions may be made to the embodiments without departing from the spirit of the invention. Accordingly, the foregoing description is meant to be exemplary only, and should not limit the scope of the invention as set forth in the following claims.

In the foregoing description, certain terms have been used for brevity, clearness, and understanding. No unnecessary limitations are to be inferred therefrom beyond the requirement of the prior art because such terms are used for descriptive purposes and are intended to be broadly construed. The different configurations, systems, and method steps described herein may be used alone or in combination with other configurations, systems and method steps. It is to be expected that various equivalents, alternatives and modifications are possible within the scope of the appended claims.

What is claimed is:

1. A computerized method of predicting carbon dioxide ($CO_2$) breakthrough in an anesthesia ventilator, the method comprising:
    inputting into a computing system a minimum detectable inspired $CO_2$ concentration ($FiCO_2$) threshold and a $CO_2$ absorbent replacement threshold;
    inputting into the computing system a set of data received from the anesthesia ventilator, wherein the set of data includes a measured $FiCO_2$;
    determining whether the measured $FiCO_2$ exceeds the minimum detectable $FiCO_2$ threshold;
    extrapolating a number of breaths for the measured $FiCO_2$ to reach the $CO_2$ absorbent replacement threshold; and
    calculating a $CO_2$ absorbent replacement time with the number of breaths and a breaths interval time.

2. The method of claim 1, further comprising the computing system outputting the CO2 absorbent replacement time to a user interface.

3. The method of claim 2, wherein the $CO_2$ absorbent replacement time is outputted to a display.

4. The method of claim 2, further comprising the computing system outputting a set of current ventilator parameter values and a set of fresh gas delivery parameter values.

5. The method of claim 2, further comprising repeating the inputting into the computing system the set of data received from the anesthesia ventilator after outputting the $CO_2$ absorbent replacement time when an anesthesia case is not complete.

6. The method of claim 1, wherein the set of data received from the anesthesia ventilator further includes an average patient expired gases ($FeCO_2$), a volume per breath of fresh gas (Vfg), and a tidal volume per breath (VT).

7. The method of claim 1, further comprising updating a $CO_2$ depletion model and computing a set of constants that illustrate a measured $FiCO_2$ response after the measured $FiCO_2$ exceeds the minimum detectable $FiCO_2$ threshold.

8. The method of claim 1, further comprising
inputting at least one what-if ventilation parameter value wherein the what-if ventilation parameter value is different from the set of data from the anesthesia ventilator; and
calculating an adjusted absorbent replacement time.

9. A non-transitory computer readable medium including instructions that, when executed on a computing system, cause the computing system to:
receive from a user interface a minimum detectable inspired $CO_2$ concentration ($FiCO_2$) threshold and a $CO_2$ absorbent replacement threshold;
receive a set of data from the anesthesia ventilator, wherein the set of data includes a measured $FiCO_2$;
determine whether the measured $FiCO_2$ exceeds the minimum detectable $FiCO_2$ threshold;
extrapolate a number of breaths for the measured $FiCO_2$ to reach the $CO_2$ absorbent replacement threshold; and
calculate a $CO_2$ absorbent replacement time with the number of breaths and a breaths interval time.

10. The medium of claim 9, further comprising the instructions causing the computing system to output the $CO_2$ absorbent replacement time to a user interface.

11. The medium of claim 10, wherein the $CO_2$ absorbent replacement time is outputted to a display.

12. The medium of claim 10, further comprising the instructions causing the computing system to output a set of current ventilator parameter values and a set of fresh gas delivery parameter values.

13. The medium of claim 10, further comprising the instructions causing the computing system to repeat the step of receiving the set of data from the anesthesia ventilator after outputting the $CO_2$ absorbent replacement time when an anesthesia case is not complete.

14. The medium of claim 10, wherein the set of data received from the anesthesia ventilator further includes an average patient expired gases ($FeCO_2$), a volume per breath of fresh gas (Vfg), and a tidal volume per breath (VT).

15. The medium of claim 10, further comprising the instructions causing the computer system to update a $CO_2$ depletion model and compute a set of constants that illustrate a measured $FiCO_2$ response after the measured $FiCO_2$ exceeds the minimum detectable $FiCO_2$ threshold.

16. The medium of claim 9, further comprising the instructions causing the computing system to:
receive from a user at least one what-if ventilation parameter value wherein the what-if ventilation parameter value is different from the set of data from the anesthesia ventilator; and
calculate an adjusted absorbent replacement time.

17. An anesthesia ventilator, comprising:
a $CO_2$ canister containing $CO_2$ absorbent;
a computing system including the storage device and a processor, the storage device including instructions that, when executed on the processor, cause the computing system to:
receive from a user interface a minimum detectable inspired $CO_2$ concentration ($FiCO_2$) threshold and a $CO_2$ absorbent replacement threshold for the $CO_2$ absorbent;
receive a set of data from the anesthesia ventilator, wherein the set of data includes a measured $FiCO_2$;
determine whether the measured $FiCO_2$ exceeds the minimum detectable $FiCO_2$ threshold;
extrapolate a number of breaths for the measured $FiCO_2$ to reach the $CO_2$ absorbent replacement threshold, wherein the extrapolation utilizes a set of predetermined parameters; and
calculate a $CO_2$ absorbent replacement time with the number of breaths and a breaths interval time, and output the $CO_2$ absorbent replacement time to a user interface.

18. The anesthesia ventilator of claim 17, further comprising the instructions causing the computer system to:
receive from a user at least one what-if ventilation parameter value, wherein the what-if ventilation parameter value is different from the set of data from the anesthesia ventilator; and
calculate an adjusted absorbent replacement time.

* * * * *